United States Patent [19]

O'Doherty

[11] Patent Number: 5,217,993
[45] Date of Patent: Jun. 8, 1993

[54] MONENSIN DERIVATIVES

[75] Inventor: George O. P. O'Doherty, Greenfield, Ind.

[73] Assignee: Eli Lilly and Company, Indianapolis, Ind.

[21] Appl. No.: 916,653

[22] Filed: Jul. 20, 1992

[51] Int. Cl.$^5$ .................... A61K 31/35; C07D 309/10
[52] U.S. Cl. ................................. 514/459; 549/343
[58] Field of Search ..................... 514/459; 549/343

[56] References Cited

U.S. PATENT DOCUMENTS 4,542,027  9/1985  Clark .................................. 549/343

Primary Examiner—C. Warren Ivy
Assistant Examiner—A. A. Owens
Attorney, Agent, or Firm—Kathleen R. S. Page; Leroy Whitaker

[57] ABSTRACT

The present invention is directed to a class of novel C-25-monohydrazine derivatives, and C-25, C-26-bishydrazine derivatives, of the polyether monensin. The derivatives are useful in animal husbandry.

27 Claims, No Drawings

MONENSIN DERIVATIVES

BACKGROUND OF THE INVENTION

The discovery of monensin was a significant one. It was the first member of what is now recognized as a class of "polyether" antibiotics. Under the trademark "Coban®", it is sold as an anticoccidial for use in chickens and turkeys. It is one of the most widely used anticoccidials, the world over. Under the trademark "Rumensin®", it is sold for use in ruminants, where its effect is to alter the rumen flora, favoring production of propionate over acetate, and thereby achieving increased growth and improved feed efficiency. The relevant patents are U.S. Pat. No. 3,501,568, regarding the compound and its anticoccidial use; and U.S. Pat. No. 3,839,557, regarding use in ruminants. U.S. Pat. No. 3,839,557 is incorporated herein by reference.

The structure of monensin has been known for a long time, and some derivatives have been prepared. None has been the subject of any commercial level of interest.

BRIEF SUMMARY OF THE INVENTION

The present invention is directed to novel derivatives of monensin. This derivatization is at the C-25 position, and additionally in some of the derivatives, at the C-26 position. The compounds of the present invention can be defined by the following structural formula:

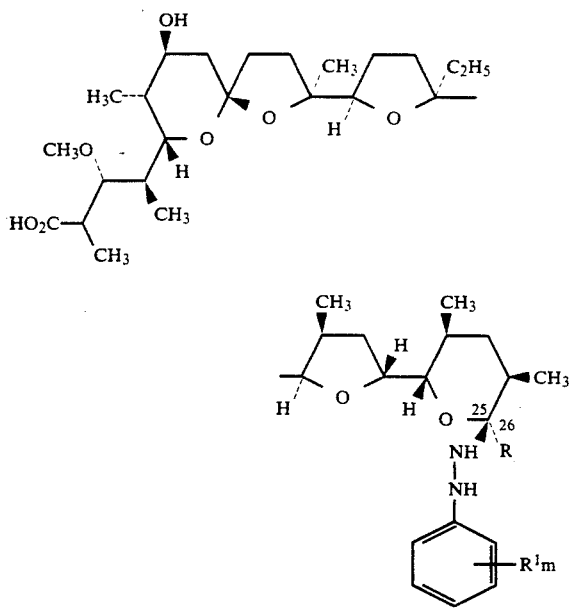

wherein R represents —CH$_2$OH or

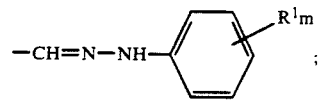

each R$^1$ independently represents halo, nitro, lower alkyl of from 1 to 3 carbon atoms, perfluoroalkyl of from 1 to 3 carbon atoms, 1,1,2,2-tetrafluoroethyl, lower alkoxy of from 1 to 3 carbon atoms, perfluoroalkoxy of from 1 to 3 carbon atoms, 1,1,2,2-tetrafluoroethoxy, or cyano, and each m independently represents an integer of from 0 to 5, with the limitation that if any one R$^1$ is other than halo, then m on that ring is an integer of from 1 to 3, only; or a physiologically acceptable salt thereof.

These derivatives are useful for treatment of ruminants, in the same manner as monensin itself is used, for the alteration of the ruminant flora, and to improve growth and feed efficiency. The derivatives can also be used in lactating ruminants to increase milk production. The present derivatives are advantageous in that they have a larger safety factor than monensin; and in dairy, the present derivatives do not cause the initial depression in feed intake which has sometimes been observed with monensin. Therefore, the present invention represents a novel and unexpected discovery.

DETAILED DESCRIPTION OF THE INVENTION

The compounds of the present invention are of two sub classes, the monohydrazine derivatives (R=CH$_2$OH, as in monensin itself) and the bishydrazine derivatives

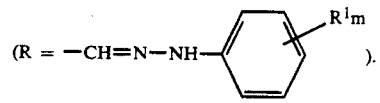

Compounds of both sub classes exist in equilibrium with ring-opened structures. For the monohydrazine compounds, the equilibrium is as follows:

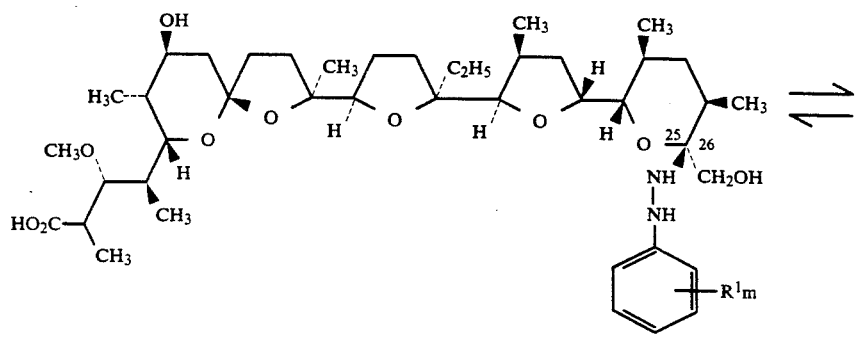

-continued

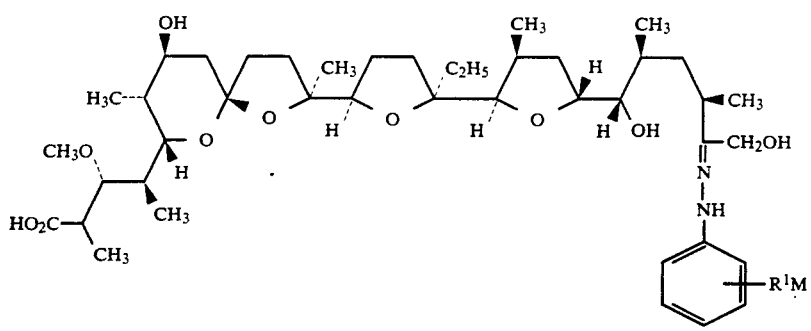

For the bishydrazine derivatives, the equilibrium is as follows:

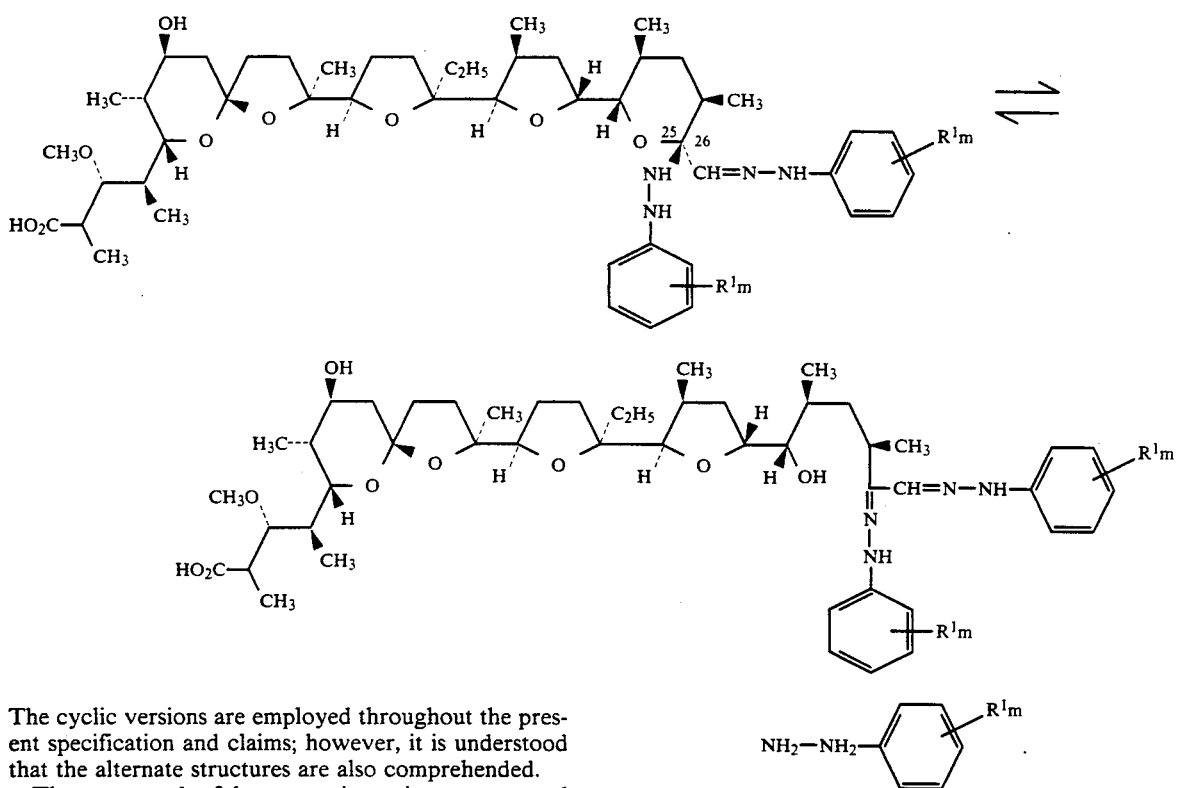

The cyclic versions are employed throughout the present specification and claims; however, it is understood that the alternate structures are also comprehended.

The compounds of the present invention are prepared by reacting monensin, either as the acid

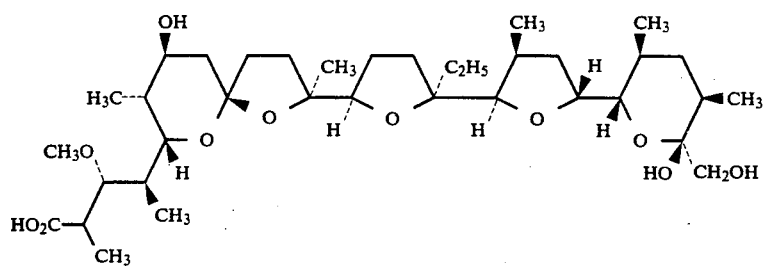

or as a suitable salt, typically the sodium salt, with a phenylhydrazine of the formula The reaction is conveniently carried out in a suitable reaction medium, such as an alkanol, acetic acid, DMF, DMSO, or the like. The reaction proceeds over a wide range of temperatures, such as 0° to 100° C., but there is no advantage with elevated or reduced temperatures, and the reaction is typically carried out at ambient room temperatures of about 10° to 25° C. The reaction consumes the reactants in equimolar amounts. Some minor experimentation may be needed to obtain either the mono or bis product to the exclusion of the other. In general, the mono product is favored by the use of monensin as the free acid, with a slight excess of the hydrazine, in ethanol. The bis product is favored by using monensin as the sodium salt, with a minimum of three moles of the hydrazine, in acetic acid.

The product is typically obtained as the free acid, but can be converted to any desirable physiologically acceptable salt by procedures well known to those skilled in the art. Salt formation occurs principally at the carboxylic acid. Suitable salts include the alkali metals such as sodium, potassium, and lithium; the alkaline earth metals such as calcium; other inorganic bases; and organic bases such as primary, secondary and tertiary lower alkyl (of $C_1$–$C_4$) amines. Such salts are prepared in standard procedures, by reacting the derivatives of the present invention in the acid form, with an appropriate base. Typically, the acid is dissolved in a suitable solvent and a solution of the desired base is added. The salt is separated in conventional procedures.

The present invention is illustrated by the following examples.

EXAMPLE 1

Monensin C-25-Phenylhydrazine Derivative, Sodium Salt

Monensin acid (0.67 gram; 0.001 mole) and phenylhydrazine (0.2 ml; 0.002 mole) were dissolved in 10 ml of ethanol and allowed to stand at 25° C. for 16 hours. TLC (ethanol:ethyl acetate, 1:9) showed no residual monensin.

The reaction mixture was diluted with about 50 ml of diethyl ether and washed sequentially with 2NHCl, water, and sodium bicarbonate solution. The washed mixture was then evaporated to dryness. Diethyl ether (5 ml) was added to the residue and chilled and filtered to obtain the product residue. Preparative TLC (ethyl acetate:ethanol, 9:1) gave 200 mg of one spot material. It melted at 140° C. Elemental analysis showed:

|  | Calculated | Found |
| --- | --- | --- |
| Carbon | 66.38 | 66.60 |
| Hydrogen | 8.89 | 8.17 |
| Nitrogen | 3.69 | 3.27 |

The identity of the product was confirmed by mass spectroscopy, which showed an ion of 783 (M+1+22 sodium).

The reaction was repeated on a larger scale, yielding product melting at 142°–144° C.

EXAMPLES 2 AND 3

Monensin C-25-(p-Nitrophenyl)Hydrazine Derivative and C-25, C-26-Bis((p-Nitrophenyl)Hydrazine) Derivative, Both as Sodium Salt Monensin sodium salt (700 mg; 0.001 mole) and (p-nitrophenyl)hydrazine (500 mg; 0.003 mole) in 10 ml of acetic acid were reacted and worked up as described in Example 1, yielding monensin C-25-(p-nitrophenyl)hydrazine derivative. Its identity was confirmed by mass, infrared and NMR spectroscopy. The remaining reaction mixture was chromatographed over silicone dioxide using ethyl acetate:ethanol, 9:1, yielding a deep yellow material which crystallized from ethyl acetateS-kellysolve B. The product melted at 208°–212° C., with decomposition. Its identity as the bis derivative, monensin C-25, C-26-bis((p-nitrophenyl)hydrazine) derivative, sodium salt, was confirmed by mass, infrared and NMR spectroscopy.

EXAMPLE 4

Monensin C-25-(p-(Trifluoromethyl)Phenyl)Hydrazine Derivative, Sodium Salt

Monensin acid (3.3 gm.; 0.005 mole) and (p-(trifluoromethyl)phenyl)hydrazine (1.0 gm; 0.006 mole) in 30 ml of ethanol were reacted and worked up as described in Example 1. Mass spectroscopy of the product showed an ion of M+1=851.

EXAMPLE 5

Monensin C-25-(p-Methoxyphenyl)Hydrazine Derivative, Sodium Salt

Monensin sodium salt (3.5 gm; 0.005 mole) and (p-methoxyphenyl)hydrazine hydrochloride (3.0 gm; 0.02 mole) in 50 ml of acetic acid were reacted and the reaction mixture worked up as described in Example 1. The desired product was obtained as an amorphous yellow brown powder melting at 140°–145° C., and exhibiting on mass spectroscopy an ion of M+1=790.

EXAMPLE 6

Monensin C-25, C-26-Bis(p-(Trifluoromethyl)Phenyl)Hydrazine Derivative, Sodium Salt Monensin sodium salt (3.5 gms; 0.005 mole) and (p-(trifluoromethyl)phenyl)hydrazine (3.0 gms; 0.018 mole) in 50 ml of acetic acid were reacted and the reaction mixture worked up as described in Example 1. The desired product was obtained as a yellow solid, melting at 180°–185° C., and exhibiting on mass spectroscopy an ion of M+1=1005.

EXAMPLE 7

Monensin C-25, C-26-Bis(Phenylhydrazine) Derivative, Sodium Salt

Monensin sodium salt (0.7 gm; 0.001 mole) and phenylhydrazine (1 ml; 0.01 mole) in acetic acid were reacted and the reaction mixture worked up as described in Example 1. The product was a pale yellow solid melting at 204° C. Elemental analysis showed the following:

|  | Calculated | Found |
| --- | --- | --- |
| Carbon | 64.62 | 64.91 |
| Hydrogen | 8.59 | 8.89 |
| Nitrogen | 6.28 | 6.57 |

Mass spectroscopy (Field Desorption) showed an ion of M+1=870.

EXAMPLE 8

Monensin C-25, C-26-Bis(p-Bromophenyl)Hydrazine Derivative, Sodium Salt

Monensin sodium salt (3.5 gm; 0.005 mole) and p-bromophenylhydrazine hydrochloride (1.5 gm; 0.007 mole) were mixed in acetic acid and the mixtured stirred at 25° C. for 3 days. The reaction mixture was then worked up as described in prior examples, yielding the product as a yellow crystalline solid which sintered at 155° C. and melted at 170° C. Mass spectroscopy showed an ion of 1029 (M+1). Elemental analysis showed:

|  | Calculated | Found |
|---|---|---|
| Carbon | 55.85 | 56.03 |
| Hydrogen | 6.62 | 6.76 |
| Nitrogen | 5.49 | 5.45 |

The compounds of the present invention are useful in animal husbandry, in ruminants grown for meat or maintained for the production of milk or other products. The present compounds provide improved growth and feed efficiency in animals grown for meat production. The compounds also alleviate and/or prevent bloat. In lactating ruminants, the present compounds improve feed efficiency and provide an enhanced energy supply to meet the demands of lactation. The compounds thereby alleviate and/or prevent ketosis.

The present compounds can be employed in a number of ruminant species. The most prominant species are cattle, sheep, and goats.

The present compounds are administered in amounts which are effective. Such amounts will vary widely with the species, the age of the animal, the specific effect desired, and other factors known to those in animal husbandry. In general, effective amounts are in the range of from 0.25 to 1.0 milligram per kilogram of animal body weight. In many situations, lesser amounts of from 0.3 to 0.4 milligram per kilogram of body weight will suffice.

The present compounds exert their effects on animals via the intestinal tract and its contents, therefore the compounds are preferably administered orally. The exact manner is not critical. The compounds can be formulated in tablets, drenches, boluses, or capsules. The compounds can also be administered via the drinking water of animals.

However, the preferred method of administering the present compounds is in the animal's normal feed. The usual practice in the industry is to prepare a concentrated premix, comprising one or more physiologically acceptable carriers, as well as the active agent. The active agent is desirably present in a concentration of from 0.5 to 50 percent, preferably from 10 to 25 percent. Such a premix is convenient for sale and distribution, whereupon it is diluted with nutritive substances, trace vitamins and minerals, and other normal components of animal feedstuffs. The result can be a final feed which is actually fed to animals. In such a final feed, a compound of the present invention is typically present in a concentration of 5-120 grams/ton, and often 10-30 grams/ton. The result can also be a somewhat more concentrated composition containing the compound of the present invention which is spread across the top of a normal animal feed as a "top dress." Many other techniques and formulations for delivering materials to animals are well known in the field of animal husbandry.

The compounds of the present invention were evaluated in a number of tests.

Batch Fermentor Tests

This test is carried out in vitro in a fermentation flask which mimics the action of the rumen, and the effect of the test is measured by analytical determination of the amounts of acetate, propionate and butyrate in the rumen fluid. The test is carried out as follows.

Rumen fluid is obtained from a steer which has a surgically-installed fistula opening into the rumen. The steer is maintained on essentially the following ration:

| Ingredient | Percentage |
|---|---|
| coarse ground corn | 40.89 |
| ground corncobs | 35 |
| soybean meal (50% protein) | 8.1 |
| alfalfa meal | 4 |
| molasses | 10 |
| urea | 0.65 |
| dicalcium phosphate | 0.6 |
| calcium carbonate | 0.3 |
| salt | 0.3 |
| Vitamin A and $D_2$ premix | 0.07 |
| Vitamin E premix | 0.05 |
| trace mineral premix | 0.04 |

Tests employing fluid from a steer on this ratio are referred to as "monensin naive." Other tests are carried out with fluid from a steer on a like ratio except that the ration contains monensin at 11 ppm. These tests are referred to as "monensin adapted."

A sample of either rumen fluid is strained through four layers of cheesecloth and the eluate is collected in a vacuum bottle. The particulate matter retained by the cheesecloth is resuspended in enough physiological buffer to return it to the original volume of the rumen fluid, and the eluate is strained again. The buffer used is described below:

| Component | grams/liter |
|---|---|
| $Na_2HPO_4$ | 0.316 |
| $KH_2PO_4$ | 0.152 |
| $NaHCO_3$ | 2.260 |
| $KCl$ | 0.375 |
| $NaCl$ | 0.375 |
| $MgSO_4$ | 0.112 |
| $CaCl_2$ | 0.038 |
| $FeSO_4.7H_2O$ | 0.008 |
| $MnSO_4$ | 0.004 |
| $ZnSO_4.7H_2O$ | 0.004 |
| $CuSO_4.5H_2O$ | 0.002 |
| $CoCl_2$ | 0.001 |

This buffer is described by Cheng et al., *J. Dairy Sci.* 38, 1225 (1955).

The two eluates are pooled in a separatory funnel, diluted 1:1 with the same buffer, and adjusted to pH 7.0 with HCl or NaOH.

Ten ml of the diluted rumen fluid prepared above is placed in a 25 ml flask with 100 mg of the same feed shown above. The compound to be tested is added to the feed, in sufficient quantity to give the concentrations of test compound in the flask which are listed in the tables below. Three replicate flasks are used per treatment.

Two sets of three untreated control flasks each are also prepared. One set of control flasks is incubated for 16 hours at 38° C. with the test flasks. The other set of three untreated control flasks are zero-time controls, to which 1 ml of 25 percent metaphosphoric acid is added as soon as the flasks are prepared to stop the fermentation.

Fermentation in the incubated test and control flasks is stopped at the end of 16 hours or 24 hours by addition of 1 ml of 25 percent metaphosphoric acid to each flask.

All of the samples are centrifuged at 3000 RCF, and the supernatant is analyzed by gas chromatographic methods for acetate, propionate, and butyrate.

The data are reported as the molar percent of the acetic, propionic, and butyric acid produced in the various flasks.

TABLES 1-11 BATCH FERMENTOR TEST DATA

TABLE 1

(monensin naive)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 67.04 | 21.01 | 11.95 |
| 16 hr) | — | 69.60 | 21.85 | 8.56 |
| 1 | 5 | 65.25 | 25.86 | 8.90 |
| | 1 | 68.21 | 22.45 | 9.34 |
| | 0.2 | 69.77 | 21.65 | 8.59 |
| 3 | 5 | 67.09 | 23.54 | 9.37 |
| | 1 | 69.22 | 21.15 | 9.63 |
| | 0.2 | 68.74 | 21.57 | 9.69 |
| 4 | 5 | 66.00 | 25.28 | 8.72 |
| | 1 | 67.11 | 23.35 | 9.54 |
| | 0.2 | 66.72 | 22.93 | 10.35 |
| 6 | 5 | 67.65 | 23.07 | 9.28 |
| | 1 | 70.14 | 21.07 | 8.79 |
| | 0.2 | 68.48 | 21.87 | 9.65 |
| 7 | 5 | 66.54 | 23.69 | 9.77 |
| | 2 | 69.64 | 20.96 | 9.40 |
| | 0.2 | 70.59 | 20.35 | 9.06 |
| monensin | 5 | 64.52 | 25.59 | 9.89 |
| | 1 | 63.91 | 25.87 | 10.22 |
| | 0.2 | 68.85 | 21.65 | 9.50 |

TABLE 2

(monensin naive)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 74.79 | 19.12 | 6.09 |
| 16 hr) | — | 63.60 | 23.98 | 12.41 |
| 1 | 3 | 63.90 | 25.19 | 10.91 |
| | 1 | 67.19 | 22.18 | 10.63 |
| | 0.3 | 66.19 | 22.28 | 11.53 |
| 3 | 3 | 66.95 | 22.62 | 10.42 |
| | 1 | 65.21 | 23.42 | 11.37 |
| | 0.3 | 66.21 | 22.23 | 11.56 |
| 4 | 3 | 65.55 | 24.30 | 10.15 |
| | 1 | 63.86 | 24.81 | 11.32 |
| | 0.3 | 67.31 | 21.73 | 10.96 |
| 6 | 3 | 65.97 | 23.29 | 10.75 |
| | 1 | 67.38 | 22.12 | 10.50 |
| | 0.3 | 67.71 | 21.36 | 10.93 |
| 7 | 3 | 66.53 | 23.14 | 10.33 |
| | 1 | 68.69 | 21.17 | 10.14 |
| | 0.3 | 68.31 | 20.77 | 10.92 |
| monensin | 3 | 62.91 | 26.45 | 10.64 |
| | 1 | 67.66 | 22.44 | 9.90 |
| | 0.3 | 69.13 | 20.51 | 10.37 |

TABLE 3

(monensin naive)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 76.66 | 17.29 | 6.85 |
| 16 hr) | — | 71.65 | 20.81 | 8.34 |

TABLE 3-continued (monensin naive)

| Compound of Example | Dose, mcg/ml | Volatile Fatty Acid Produced | | |
|---|---|---|---|---|
| | | Acetic (molar %) | Propionic (molar %) | Butyric (molar %) |
| 5 | 20 | 69.85 | 22.62 | 7.52 |
| | 10 | 70.36 | 21.34 | 8.29 |
| | 5 | 71.04 | 20.78 | 8.18 |

TABLE 4

(monensin adapted)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 71.56 | 19.83 | 8.60 |
| 16 hr) | — | 69.98 | 20.39 | 10.64 |
| 1 | 5 | 64.21 | 26.05 | 9.74 |
| | 5 | 67.86 | 22.61 | 9.53 |

TABLE 5

(monensin adapted)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 71.02 | 20.65 | 8.32 |
| 16 hr) | — | 68.10 | 20.65 | 11.25 |
| 1 | 10 | 65.23 | 25.14 | 9.62 |
| | 5 | 67.22 | 23.30 | 9.48 |
| | 2.5 | 67.04 | 22.45 | 10.51 |
| | 1 | 67.06 | 21.54 | 11.40 |
| 1 | 10 | 67.53 | 22.56 | 9.92 |
| | 5 | 67.35 | 21.51 | 11.14 |
| | 2.5 | 67.75 | 21.36 | 10.89 |
| | 1 | 67.13 | 20.98 | 11.89 |

TABLE 6

(Experiment # RL-5905)
(monensin adapted)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 71.43 | 22.43 | 6.14 |
| 16 hr) | — | 66.37 | 23.36 | 10.27 |
| 1 | 10 | 63.35 | 27.03 | 9.61 |
| | 10 | 58.15 | 33.16 | 8.69 |

TABLE 7

(monensin adapted)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 70.15 | 23.68 | 6.18 |
| 16 hr) | — | 64.47 | 24.20 | 11.32 |
| 1 | 5 | 62.49 | 27.36 | 10.14 |
| | 5 | 57.55 | 32.81 | 9.65 |

TABLE 8

(monensin adapted)
(Comparing different lots of the compound of Example 1)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 71.47 | 22.31 | 6.22 |
| 16 hr) | — | 66.09 | 22.98 | 10.93 |
| 1 | 5 | 56.51 | 33.18 | 10.31 |
| | 5 | 62.67 | 27.96 | 9.37 |
| | 5 | 61.32 | 27.92 | 10.76 |
| | 5 | 63.96 | 25.43 | 10.61 |
| | 5 | 56.04 | 33.21 | 10.75 |

TABLE 9

(monensin adapted)
(Comparing different lots of the compound of Example 1)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 71.63 | 21.63 | 6.75 |
| 16 hr) | — | 66.29 | 23.05 | 10.67 |
| 1 | 10 | 60.82 | 30.81 | 8.37 |
| | 5 | 63.01 | 27.47 | 9.52 |
| | 2.5 | 63.14 | 27.61 | 9.24 |
| | 1 | 66.35 | 23.98 | 9.75 |
| 1 | 10 | 65.16 | 24.65 | 10.19 |
| | 5 | 65.16 | 23.92 | 10.92 |
| | 2.5 | 60.04 | 29.82 | 10.14 |
| | 1 | 64.60 | 25.65 | 9.75 |
| 1 | 10 | 65.05 | 25.07 | 9.87 |
| | 5 | 65.32 | 24.09 | 10.59 |
| | 2.5 | 65.10 | 25.03 | 9.87 |
| | 1 | 65.28 | 24.09 | 10.64 |
| 1 | 10 | 61.16 | 30.11 | 8.73 |
| | 5 | 62.05 | 28.72 | 9.23 |
| | 2.5 | 62.87 | 27.72 | 9.41 |
| | 1 | 62.06 | 27.14 | 10.80 |
| 1 | 10 | 54.35 | 35.68 | 9.97 |
| | 5 | 56.35 | 32.87 | 10.78 |
| | 2.5 | 60.31 | 29.79 | 9.91 |
| | 1 | 65.16 | 25.35 | 9.48 |

TABLES 10

(monensin naive)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 73.7 | 16.9 | 9.5 |
| 24 hr) | — | 72.0 | 18.3 | 9.6 |
| 2 | 10 | 67.3 | 24.0 | 8.7 |
| | 5 | 68.2 | 23.0 | 8.8 |
| | 2.5 | 70.1 | 20.5 | 9.4 |
| 8 | 10 | 71.6 | 19.9 | 9.7 |
| | 5 | 71.6 | 18.8 | 9.5 |
| | 2.5 | 71.3 | 18.8 | 9.8 |
| monensin | 5 | 67.0 | 24.6 | 8.4 |

TABLE 11

(monensin naive)

| Compound of Example | Dose, mcg/ml | Volatile Fatty Acid Produced | | |
|---|---|---|---|---|
| | | Acetic (molar %) | Propionic (molar %) | Butyric (molar %) |
| (controls at: | | | | |
| 0 hr | — | 72.7 | 17.8 | 9.4 |
| 24 hr) | — | 71.3 | 19.0 | 9.6 |
| 2 | 10 | 67.3 | 23.9 | 8.8 |
| | 5 | 68.2 | 22.6 | 9.0 |
| | 2.5 | 70.1 | 20.8 | 9.4 |
| monensin | 5 | 67.1 | 24.4 | 8.4 |

The foregoing tables demonstrate that the compounds of the present invention elevate propionic acid production.

Continuous Fermentor Tests

The compounds of the present invention were also evaluated in continuous fermentation flasks.

These continuous fermentation flasks mimic the action of the rumen over a long period of time. Each flask was a gas-tight container having liquid inlet ports, solid inlet ports, sampling ports and gas exit tubes leading to rubber bladders which receive the gases produced by the fermentation. The liquid volume in each flask was controlled at 550 ml by a stand pipe leading to a liquid collection vessel. The temperature of the flasks was controlled at 38°–40° C. Each flask was gently stirred by a magnetic stirrer.

Each experiment was started by adding to a flask 550 ml of strained rumen fluid obtained from a fistulated steer which had been fed the same diet used in the batch fermentor test. The effluent collection flask was precharged with 50 ml of dilute metaphosphoric acid, to stop fermentation in the liquid overflowing from the flask. The flask was sealed, and the gas collection bladders were attached.

A buffer, pH 6.8–7.0, was added to each flask continuously. The buffer had the following composition:

| Component | grams/liter |
|---|---|
| Sodium hydrogen phosphate | 2.2 |
| Magnesium chloride | 0.036 |
| Sodium bicarbonate | 5.9 |
| Potassium chloride | 0.34 |
| Sodium chloride | 0.28 |
| Urea | 1.0 |
| Calcium chloride | 0.024 |

The buffer was added at the rate of 875 ml/day.

A 10 g addition of the appropriate feed was added twice daily through the feeding port to each flask, for 7 days. After each feeding, the gas outlet port was closed off and the flask was flushed with carbon dioxide Each day, the effluent liquid was collected and analyzed, and the gas which left the flask was collected and analyzed.

The compound was added to the feed in amounts suitable to give the concentration of compound in the 875 ml liquid dynamic volume of the flask which is shown in the tables below.

Acetate, propionate and butyrate data were obtained on the effluent liquid from each flask. The effluent gas from each flask was analyzed for methane. Methane inhibition contributes to more efficient feed utilization in ruminants by diverting the acetate to usable energy rather than to methane which is expelled.

In most tests, 2 flasks were used for each treatment level of each compound, and the data from both flasks from all treatment days were pooled and averaged.

The table below reports data obtained from tests in which the full flasks were fed a diet consisting of 50% hay and 50% of the mixed ration described in Test 1 above.

The results of testing selected compounds of the present invention are set forth in the following tables.

TABLES 12-14 CONTINUOUS FERMENTOR TEST DATA

TABLE 12

| Compound of Example | Conc. in mg/ liter | Molar Percent, Volatile Fatty Acids | | | $CH_4$ mmoles/ day |
|---|---|---|---|---|---|
| | | Acetic Acid | Propionic Acid | Butyric Acid | |
| (control) | — | 49.4 ± 2.2 | 41.5 ± 2.1 | 9.0 ± 0.7 | 2.8 |
| 1 | 1 | 44.3 ± 5.8 | 46.1 ± 5.1 | 9.7 ± 0.9 | 3.4 |
| monensin | 1 | 41.4 ± 8.6 | 47.8 ± 6.8 | 10.8 ± 2.0 | 2.2 |

TABLE 13

| Compound of Example | Conc. in mg/ liter | Molar Percent, Volatile Fatty Acids | | | $CH_4$ mmoles/ day |
|---|---|---|---|---|---|
| | | Acetic Acid | Propionic Acid | Butyric Acid | |
| (control) | — | 49.1 ± 1.6 | 41.9 ± 1.8 | 8.9 ± 0.7 | 4.6 |
| 4 | 1 | 44.0 ± 5.5 | 46.1 ± 4.7 | 9.8 ± 1.1 | 4.3 |
| monensin | 1 | 41.6 ± 7.9 | 48.6 ± 7.1 | 9.8 ± 1.1 | 2.3 |

TABLE 14

| Compound of Example | Conc. in mg/ liter | Molar Percent, Volatile Fatty Acids | | | $CH_4$ mmoles/ day |
|---|---|---|---|---|---|
| | | Acetic Acid | Propionic Acid | Butyric Acid | |
| (control) | — | 48.1 ± 1.1 | 42.0 ± 1.8 | 9.9 ± 1.1 | 2.2 |
| 7 | 1 | 47.3 ± 1.3 | 43.6 ± 2.4 | 9.1 ± 1.4 | 1.1 |
| monensin | 1 | 40.2 ± 8.3 | 51.2 ± 9.7 | 8.6 ± 1.7 | 2.5 |

The data in these tables further demonstrate that the compounds of the present invention elevate propionic acid production.

Premix

A premix containing the compound of Example 1 was prepared as follows: rice hulls and an anti-dusting oil were mixed in a Hobart mixer for five minutes. The compound of Example 1 was added and the mixing continued for another five minutes. This yielded a homogeneous premix of the following composition:

| | |
|---|---|
| Compound of Example 1 | .600 |
| Rice hulls | 3.891 |
| Anti-dusting oil | .045 |
| | 4.536 kg |

This premix contained the compound of Example 1 in a concentration of 13.23 percent.

Topdress

The premix was employed to make a "topdress" suitable for dairy. A portion of the premix was mixed with a standard dairy carrier of the following composition

| Component | Percent |
|---|---|
| Ground corn | 20 |
| Grit-o-cobs | 38 |
| Cane molasses | 2.5 |
| Oats | 11 |
| Soybean oil meal (48% protein) | 25 |
| Vitamin A and $D_3$ premix | 1.1 |
| Salt | 0.4 |
| Animal fat | 2 |
| | 100.0 | to obtain a topdress formulation containing 1.512 kg of premix per one thousand pounds.

Dairy Trial

The compound of Example 1 was additionally evaluated in dairy cows, including both multiparous and primiparous cows. The cows were fed a diet consisting of either 35% forage and 65% concentrate, or 50% forage and 50% concentrate (percentages on a dry matter basis).

One group of 23 cows received only these diets (10 received the 35/65 diet; 13, the 50/50 diet). Another group of 21 cows received these diets modified by addition of the topmix described above, spread over the morning feeding (11 received the 35/65 diet; 10, the 50/50 diet—both modified by the addition of the topmix). This feeding regimen provided the compound of formula I in the amount of 200 mg/head/day, or 0.36 mg per kilogram of animal body weight.

The test period, and treatment in the case of the group of cows receiving the compound of Example 1, began at least one day prepartum and continued for approximately 84 days of lactation. Milk production, feed intake, body weight, and plasma ketone concentrations were determined. Because there was no effect of diet by compound interaction, results were combined for all control animals, and for all treated animals. The results were as set forth in the following table.

TABLE 15

| DAIRY TRIAL | | |
|---|---|---|
| Parameter Measured | Control | Treatment with Compound of Example 1 |
| Milk, kg/d | 28.8 | 30.0 |
| Fat, % | 2.74 | 2.65 |
| Protein, % | 3.00 | 2.95 |
| 3.5 Fat corrected milk, kg/d | 25.2 | 25.6 |
| Dry matter intake, kg/d | 15.9 | 16.2 |
| Body weight, kg | 539 | 549 |

In the cows receiving the compound of Example 1, milk production was increased overall by 1.2 kg/d (for primiparous and multiparous cows, by 2.2 and 0.3 kg/d, respectively). Differences in milk fat and milk protein were not significant, and there was no overall effect of the compound of Example 1 on plasma ketone concentrations. Also, there were no significant differences between the control and treated groups for fat corrected milk, dry matter intake, and body weight.

I claim:

1. A compound of the formula

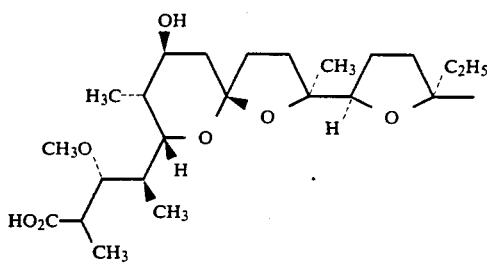

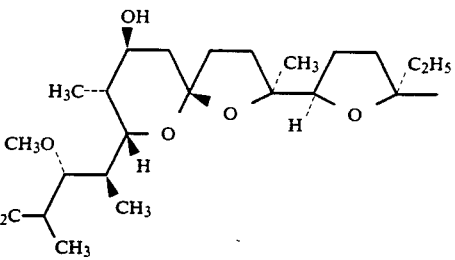

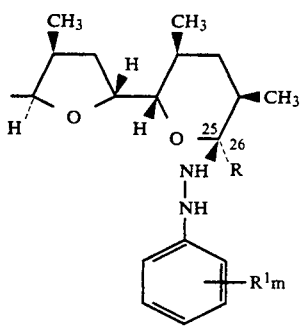

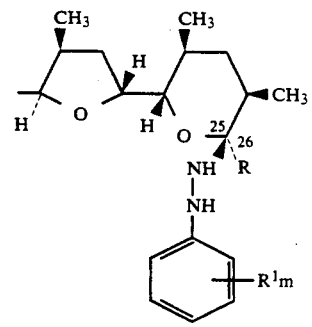

wherein R represents —CH$_2$OH or

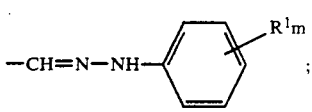

each R$^1$ independently represents halo, nitro, lower alkyl of from 1 to 3 carbon atoms, perfluoroalkyl of from 1 to 3 carbon atoms, 1,1,2,2-tetrafluoroethyl, lower alkoxy of from 1 to 3 carbon atoms, perfluoroalkoxy of from 1 to 3 carbon atoms, 1,1,2,2-tetrafluoroethoxy, or cyano, and each m independently represents an integer of from 0 to 5, with the limitation that if any one R$^1$ is other than halo, then m on that ring is an integer of from 1 to 3, only; or a physiologically acceptable salt thereof.

2. The compound of claim 1 wherein R is —CH$_2$OH.

3. The compound of claim 2 in which m=0.

4. The compound of claim 3 which is the sodium salt.

5. The compound of claim 1 wherein R is

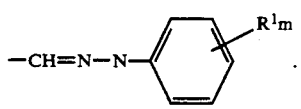

6. The compound of claim 5 in which m in both occurrences=0.

7. The compound of claim 6 which is the sodium salt.

8. A method of increasing production of propionate in the rumen of a ruminant animal which comprises orally administering to the animal an effective amount of a compound of the formula wherein R represents —CH$_2$OH or

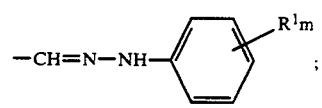

each R$^1$ independently represents halo, nitro, lower alkyl of from 1 to 3 carbon atoms, perfluoroalkyl of from 1 to 3 carbon atoms, 1,1,2,2-tetrafluoroethyl, lower alkoxy of from 1 to 3 carbon atoms, perfluoroalkoxy of from 1 to 3 carbon atoms, 1,1,2,2-tetrafluoroethoxy, or cyano, and each m independently represents an integer of from 0 to 5, with the limitation that if any one R$^1$ is other than halo, then m on that ring is an integer of from 1 to 3, only; or a physiologically acceptable salt thereof.

9. The method of claim 8 employing a compound wherein R is —CH$_2$OH.

10. The method of claim 9 in which m=0.

11. The method of claim 10 wherein the compound is the sodium salt.

12. The method of claim 8 employing a compound wherein R is

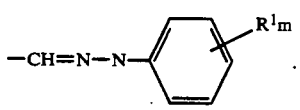

13. The method of claim 12 employing a compound wherein m in both occurrences=0.

14. The method of claim 13 wherein the compound is the sodium salt.

15. A method of increasing the production of milk in a lactating ruminant animal which comprises orally administering to the animal an effective amount of a compound of the formula

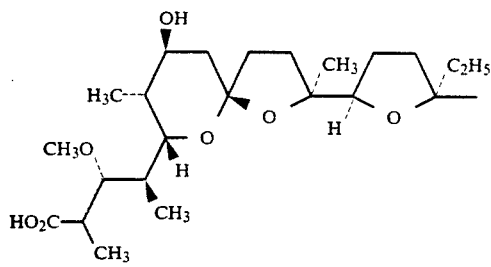

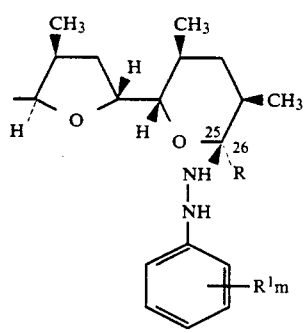

wherein R represents —CH₂OH or

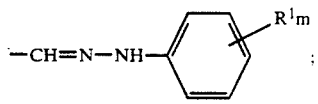

each $R^1$ independently represents halo, nitro, lower alkyl of from 1 to 3 carbon atoms, perfluoroalkyl of from 1 to 3 carbon atoms, 1,1,2,2-tetrafluoroethyl, lower alkoxy of from 1 to 3 carbon atoms, perfluoroalkoxy of from 1 to 3 carbon atoms, 1,1,2,2-tetrafluoroethoxy, or cyano, and each m independently represents an integer of from 0 to 5, with the limitation that if any one $R^1$ is other than halo, then m on that ring is an integer of from 1 to 3, only; or a physiologically acceptable salt thereof.

16. The method of claim 15 employing a compound wherein R is —CH₂OH.

17. The method of claim 16 in which m=0.

18. The method of claim 17 wherein the compound is the sodium salt.

19. The method of claim 15 employing a compound wherein R is

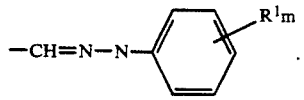

20. The method of claim 19 employing a compound wherein m in both occurrences=0.

21. The method of claim 20 wherein the compound is the sodium salt.

22. A premix for a ruminant feedstuff, which premix comprises an active ingredient which is a compound of claim 1, said active ingredient being present in a concentration of from 0.5 to 50 percent.

23. The premix of claim 22 in which the active ingredient is present in a concentration of from 10 to 25 percent.

24. The premix of claim 23 in which the active ingredient is monensin C-25-phenylhydrazine derivative, or a physiologically acceptable salt thereof.

25. An animal feedstuff suitable for administration to ruminants to increase growth and improve feed efficiency, or to increase milk production, which comprises an effective concentration of an active ingredient which is a compound of claim 1.

26. The animal feedstuff of claim 25 in which the concentration of active ingredient is from 5 to 120 grams/ton.

27. The animal feedstuff of claim 26 in which the active ingredient is monensin C-25-phenylhydrazine derivative, or a physiologically acceptable salt thereof.

* * * * *